US006888105B2

(12) United States Patent
Seibert et al.

(10) Patent No.: US 6,888,105 B2
(45) Date of Patent: May 3, 2005

(54) SOFT-SIDED ENVIRONMENTAL ENCLOSURE

(75) Inventors: Brian Seibert, Monroeville, NJ (US); Kenneth B. Carll, Bridgeton, NJ (US)

(73) Assignee: Alcan Packaging Pharmaceutical & Personal Care Inc., Millville, NJ (US)

( * ) Notice: Subject to any disclaimer, the term of this patent is extended or adjusted under 35 U.S.C. 154(b) by 0 days.

(21) Appl. No.: 10/737,337

(22) Filed: Dec. 16, 2003

(65) Prior Publication Data

US 2004/0169030 A1 Sep. 2, 2004

Related U.S. Application Data

(60) Provisional application No. 60/434,134, filed on Dec. 17, 2002.

(51) Int. Cl.[7] .......................... C12M 1/38; F27D 11/00; F27D 7/04

(52) U.S. Cl. ............................ 219/400; 219/386; 236/3

(58) Field of Search ................................ 219/400, 401, 219/385, 386; 236/3; 237/286.6, 809; 454/56

(56) References Cited

U.S. PATENT DOCUMENTS 3,577,650 A * 5/1971 Brahm ....................... 219/400
3,818,896 A 6/1974 Deaton
3,848,776 A 11/1974 Schieser
4,111,753 A 9/1978 Folsom et al.
4,213,498 A 7/1980 Vandenbossche
4,276,819 A * 7/1981 Goldman et al. ............. 454/56
4,444,183 A 4/1984 Heckendorn
4,514,993 A 5/1985 Johnson
4,537,313 A 8/1985 Workman
4,777,802 A 10/1988 Feher
4,802,344 A 2/1989 Livingston et al.
4,892,830 A 1/1990 Findley et al.
4,984,662 A 1/1991 Jacober
5,063,924 A 11/1991 Galvan et al.
5,065,879 A 11/1991 King
5,125,238 A 6/1992 Ragan et al.
5,392,847 A 2/1995 Stephenson
5,519,188 A * 5/1996 Yuichi et al. ............... 219/401
5,562,228 A 10/1996 Ericson
5,569,401 A 10/1996 Gilliland et al.
5,681,627 A 10/1997 Mueller
5,683,441 A 11/1997 Dickerhoff et al.
5,728,145 A 3/1998 Phlipot et al.
5,782,174 A 7/1998 Cohn et al.
5,792,427 A * 8/1998 Hugh et al. .................... 236/3
5,832,919 A 11/1998 Kano et al.
5,890,781 A 4/1999 Ryder
5,941,907 A 8/1999 Augustine
5,968,084 A 10/1999 Augustine et al.
5,988,876 A 11/1999 Duren
6,323,464 B1 * 11/2001 Cohn ......................... 219/401

* cited by examiner

*Primary Examiner*—Joseph Pelham
(74) *Attorney, Agent, or Firm*—RatnerPrestia

(57) ABSTRACT

A cover for a rack to control the temperature of the contents of the rack is provided. The cover comprises a frame having a heater, a soft hood with a top and a bottom, the hood extending downward from the frame, and a duct fluidly connecting the heater to the bottom of the hood whereby the duct introduces heated air into the bottom of the hood. Also included is a method of controlling the temperature of a reaction using the cover of the present invention.

15 Claims, 9 Drawing Sheets

SOFT-SIDED ENVIRONMENTAL ENCLOSURE

This application claims the benefit of U.S. P Provisional Patent Application No. 60/434,134, filed Dec. 17, 2002. The entire disclosure of U.S. Provisional Patent Application No. 60/434,134, filed Dec. 17, 2002, is expressly incorporated by reference herein.

FIELD OF THE INVENTION

The present invention is related to climate control devices, and more specifically to the control of temperature in laboratory racks and incubators.

BACKGROUND OF THE INVENTION

It is often desirable in laboratory work to have a controlled environment in which to allow experimentation to occur. This control would especially include temperature, particularly in biological experimentation and production. Several techniques have been developed to insure this control.

Many popular incubators are actually boxes which contain an atmosphere suitable for the growth of organisms. Such incubators are typically plastic or metal and consist of walls containing a variety of equipment assembled for the particular experimentation. Other types of controlled atmosphere incubators are adapted to receive a tray or rack of individual containers, reactors, or bottles in which experimentation and production are being performed. These racks are often on rollers and can be rolled into, and later out of, the controlled atmosphere enclosure.

One drawback to many of these known devices and systems is that the enclosure into which the racks are rolled take up a large amount of space, at least as much as the racks themselves. Thus, laboratory space, which is often limited and expensive, must accommodate cabinets and even, sometimes, small rooms into which bottle or reactor racks can be placed.

SUMMARY OF THE INVENTION

The present invention provides a cover for a rack to control the temperature of the rack and its contents. The invention comprises a frame having a temperature-controlling element, such as a heater or refrigeration device, a soft hood extending downward from the frame, and at least one duct fluidly connecting the temperature-controlling element to the bottom of the hood to allow passage of the temperature-controlled air from the temperature-controlling element to the bottom of the hooded environment. The rack with its contents is then placed into the soft-sided structure during experimentation so that a controlled temperature environment can be maintained.

In a preferred embodiment, the cover apparatus includes a blower in the frame to force warmed air down the duct(s) into the bottom of the hood. Preferably, the frame has four sides and the hood hangs down from the frame. The inner dimensions of the hood are only slightly larger than the outer dimensions of the rack for which it is designed to house. The frame is attached to a wall, suspended from a ceiling, or is adapted to be disposed atop the rack. Control devices are disposed on the frame to control temperature and air flow through the hooded enclosure. The duct(s) are preferably disposed outside of the shell, and most preferably they are formed integrally with the shell. Either the frame or the duct system has a cold air intake at the top to feed air to the heater.

Also included in the invention is a method of controlling the temperature of a reaction comprising the steps of suspending a soft hood from a frame to form an enclosed area below the frame, inserting a reaction vessel into the enclosed area, bringing air within the frame to a first desired temperature, passing the air from the frame to the bottom of the hood and into the enclosed area, and taking up the air from the enclosed area at the top of the hood at a second temperature back into the frame where it is again brought to the first desired temperature. The temperature within the enclosed area is monitored and controlled to maintain the desired temperature within a preset tolerance, for example 37° C.±1° C. This cycle is continued until a desired reaction is complete.

BRIEF DESCRIPTION OF THE DRAWING

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DETAILED DESCRIPTION OF THE INVENTION

The present invention provides a cover for a rack to control the temperature of the rack and its contents. The invention comprises a frame having a temperature-controlling element, a soft hood extending downward from the frame, and at least one duct fluidly connecting the temperature-controlling element to the bottom of the hood to allow passage of air from the temperature-controlling element to the bottom of the hooded environment. The rack with its contents is then placed into the soft-sided structure during experimentation and production so that a controlled temperature environment can be maintained.

The cover apparatus preferably includes a blower in the frame to force air down the duct(s) into the bottom of the hood. Preferably, the frame has four sides and the hood hangs down from the frame. The inner dimensions of the hood are only slightly larger than the outer dimensions of the rack for which it is designed to house. The frame is attached to a wall or ceiling, or is adapted to be disposed atop the rack. Control devices are disposed on the frame to control temperature and air flow through the hooded enclosure. The duct(s) are preferably disposed outside of the hood, and most preferably they are formed integrally with the hood. Either the frame or the duct system has an air intake at the top to feed air to the temperature-controlling element. Preferably, the temperature-controlling element is a heater.

Figure 1A:
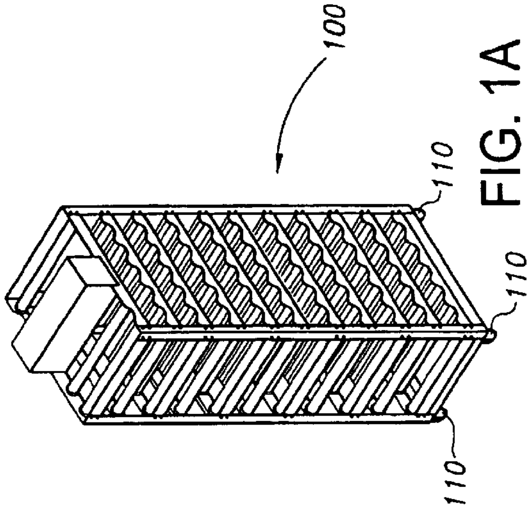
FIG. 1A is a diagonal view of a rack which can be used with the present invention.

The hood is generally designed to fit over whatever rack is used in a particular laboratory. A preferred embodiment of the invention provides a hood for a bottle rack such as that shown in FIG. 1, which keeps cell cultures at an appropriate temperature for growth. FIG. 1A shows a typical laboratory rack 100 known in the art. Generally, rack 100 is a series of decks or levels of rollers for bottles to be inserted and laid into place while a reaction occurs within the bottle. Often the rack is on wheels 110 to allow movement of the rack around the laboratory.

Figure 1B:
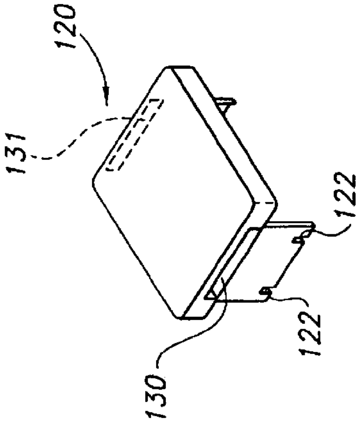
FIG. 1B is a diagonal view of one embodiment of the frame according to the present invention.

FIG. 1B shows a part of the present invention, namely frame 120 from which the hood (discussed below) can hang. Frame 120 as shown in FIG. 1B is designed to attach or otherwise sit atop rack 100. Clips 122 are provided in this particular embodiment to allow a secure attachment. Frame 120 also houses a temperature-controlling element, preferably a heater, and blower (not shown), and associated duct work to transfer warmed air from the heater to the edge of the frame at frame duct connection ports 130 and 131, as shown in FIG. 1B. This duct connection is where the duct(s) of the hood contact the frame to deliver air down the sides of the hood and into the bottom of the hooded, enclosed area, as discussed more detailedly below.

Figure 1C:
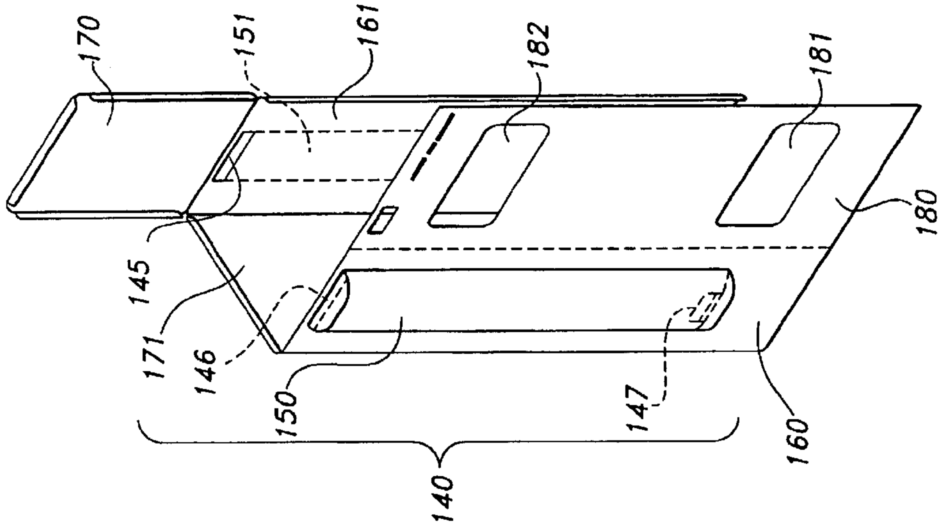
FIG. 1C is a diagonal view of one embodiment of the hood according to the present invention.

FIG. 1C illustrates a hood according to one embodiment of the present invention. In this embodiment, hood 140 is five-sided cover, made from a flexible material or layers of material. Hood duct intake connection ports 145 and 146 are shown in the top two sides of hood 140, to allow fluid connection with frame duct connection ports 130 and 131 when hood 140 is placed overtop frame 120. Hood duct output ports 147 and 148 (not shown in FIG. 1C, but see FIG. 6) are where heated air is blown into the enclosed area within hood 140. In this embodiment, two ducts, namely ducts 150 and 151, are used. Other embodiments could have a refrigeration device instead of a heater, or only one duct, or more than two ducts. It should also be noted that ducts 150 and 151 are shown disposed on the outside of sides 160 and 161 of hood 140, but the ducts may be disposed within the hood.

Figure 1D:
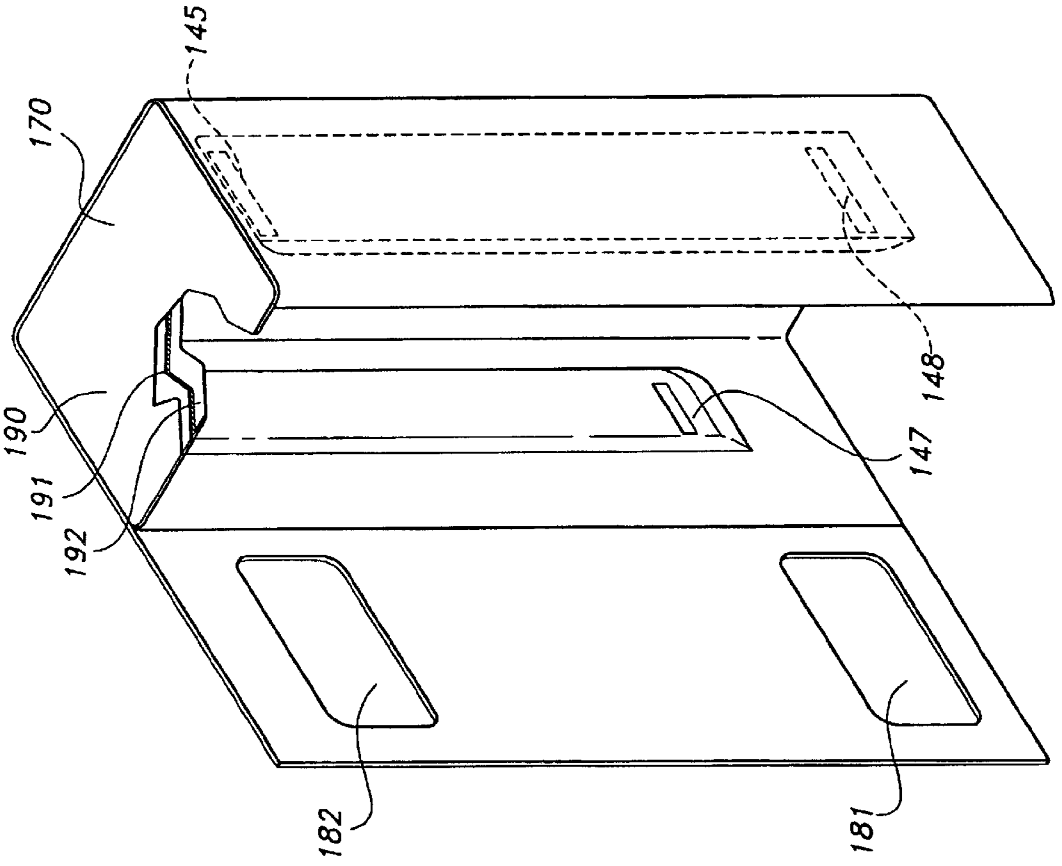
FIG. 1D is a front view of the hood having two ducts, each disposed within the hood.

FIG. 1D shows an embodiment where two ducts are present, one per side, and each is disposed within the enclosed area of the hood. The drawback of having the ducts disposed within the hood is that rack 100 will not fit as easily. The advantage, however, is that less heat is lost as warmed air is pushed down the ducts to be introduced into the bottom of the enclosed area at hood duct output ports 147 and 148. FIG. 1D also shows a cut-away section of the material of the hood in this embodiment, which is multilayered. This aspect is discussed in more detail below.

Figure 2:
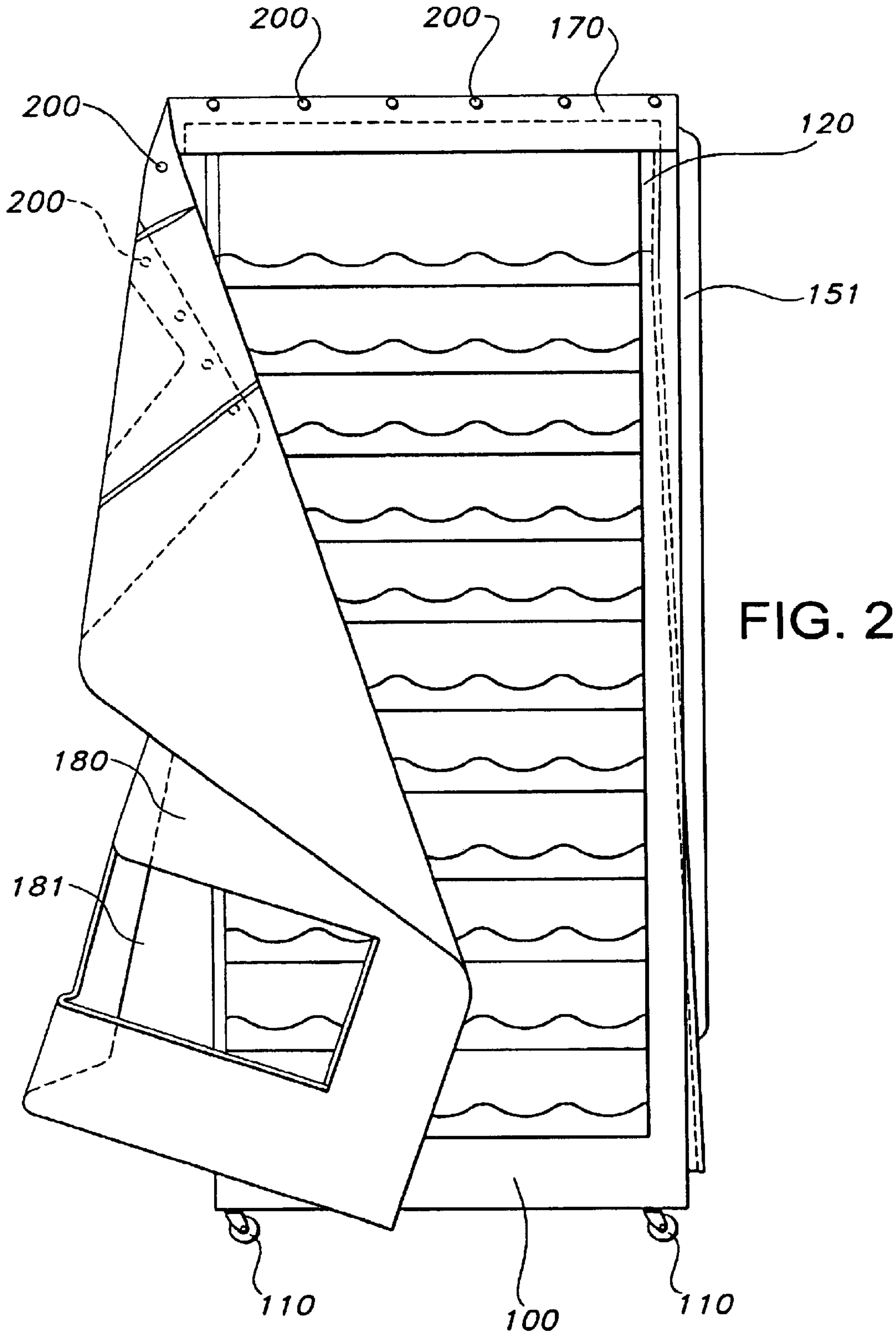
FIG. 2 is a front view of a rack disposed within one embodiment of the present invention with the front panel opened.

As noted above, hood 140, as shown in FIG. 1C, has five sides. Namely, sides 160 and 161, top 170, back 171, and front panel 180. Top 170 folds down onto the top of frame 120, rack 140 is placed into the enclosed area defined by hood 140 and the floor, and front panel 180 is closed. The unit is closed with snaps, a hook and loop fastener such as Velcro® (Velcro is a registered trademark of Velcro Industries for snap-hook fasteners), zippers, magnets, rivets, gluing, sewing, taping or other mechanical fastening methods. Certain applications may require methods that would create a seal. FIG. 2 shows snaps 200 along top 170 and front panel 180, for example. In this embodiment, front panel 180 also includes two windows, 181 and 182 for viewing the contents of the hood.

Figure 3:
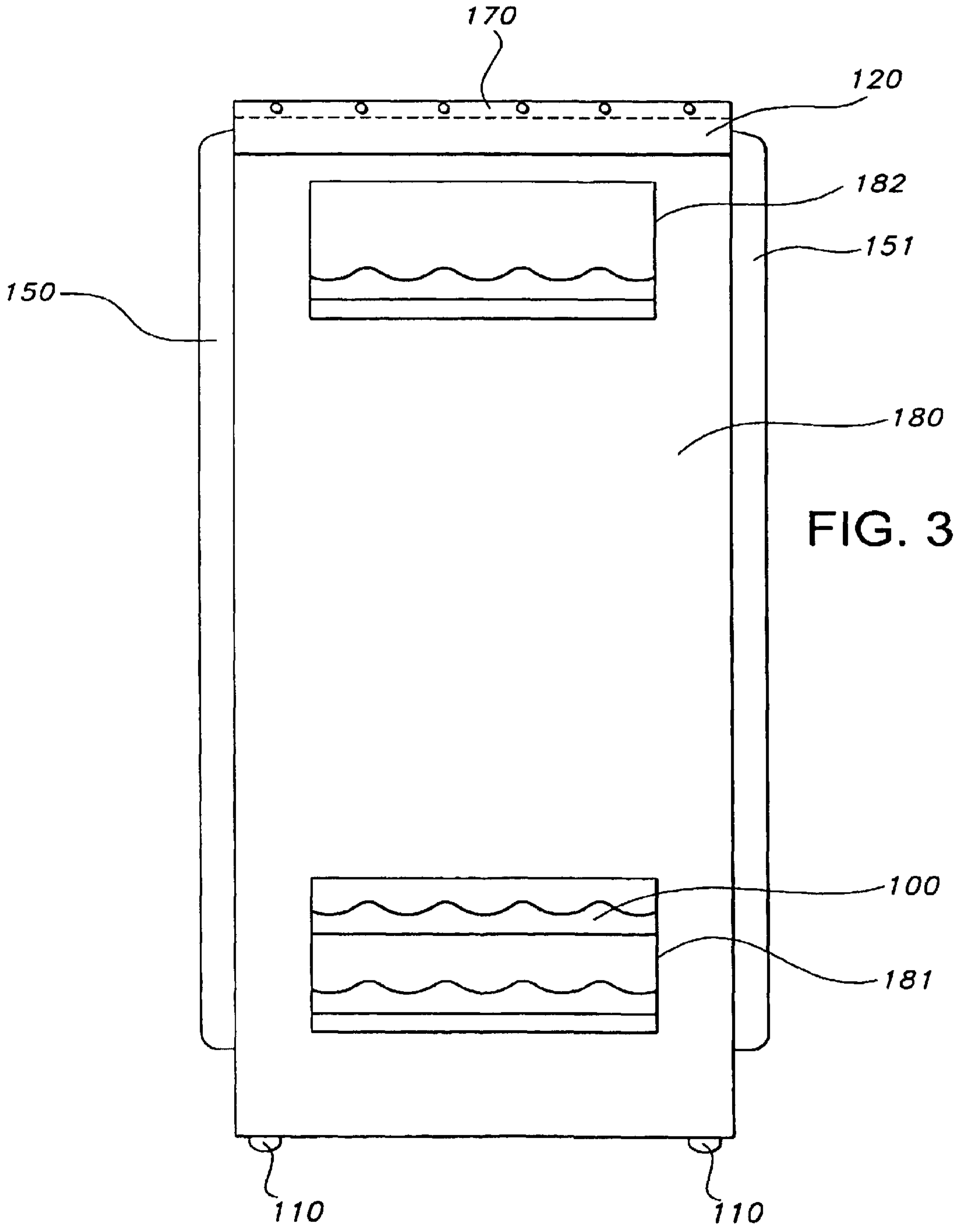
FIG. 3 is a front view of FIG. 2 with the front panel closed.
Figure 4:
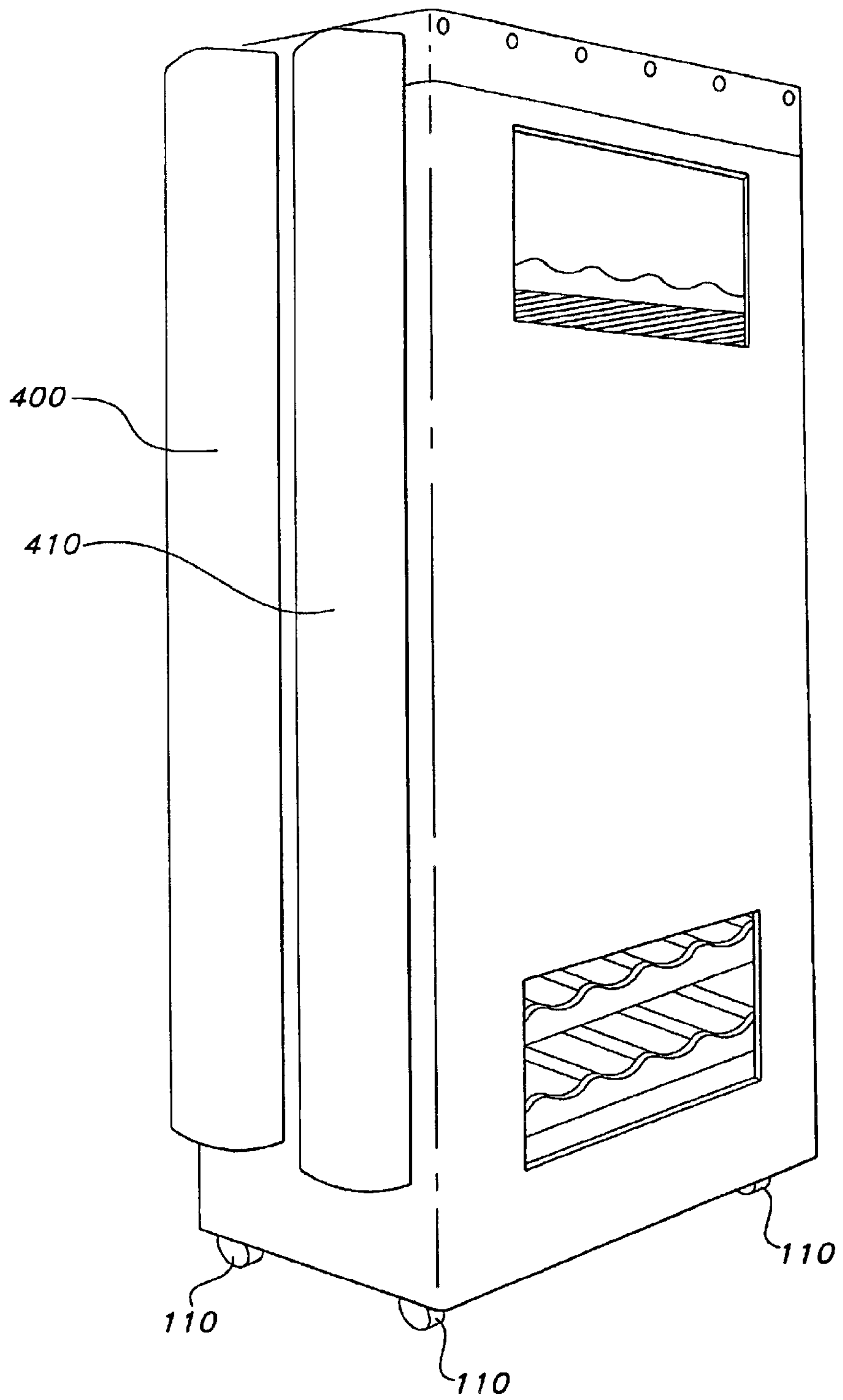
FIG. 4 is a diagonal view of an embodiment of the present invention with two ducts on one side of the hood.
Figure 5:
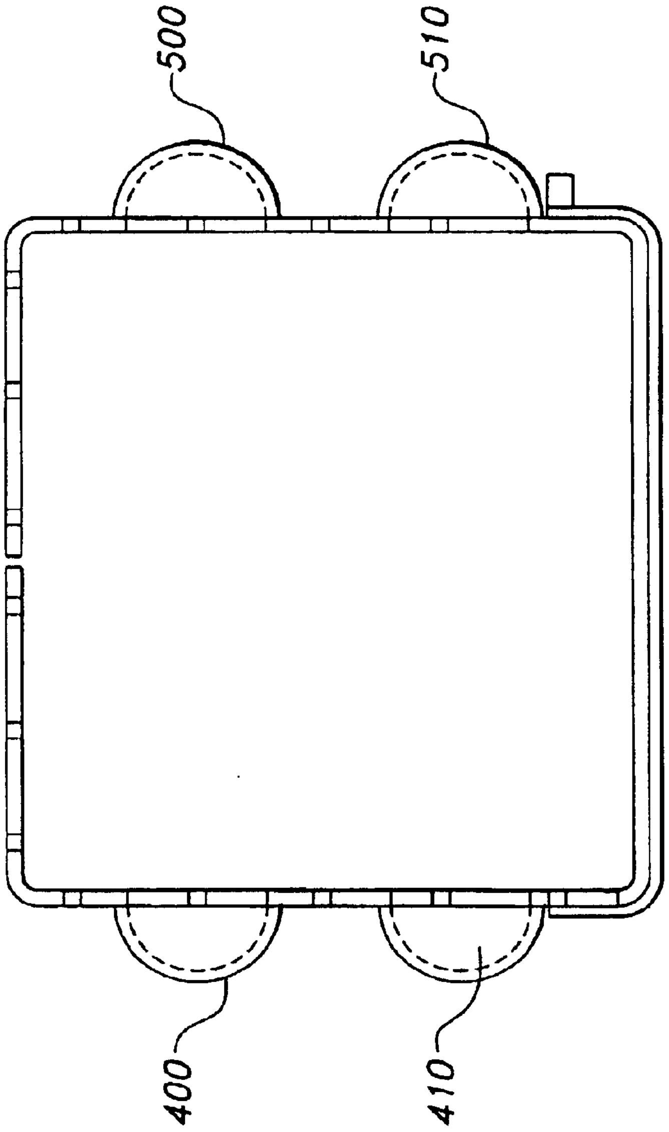
FIG. 5 is a top view of an embodiment of the present invention with two ducts per side of the hood.

FIG. 2 shows a front view of hood 140 in place over frame 120 with rack 100 disposed therein. Front panel 180 is not yet closed, and rack 100 can be seen clearly in place. FIG. 3 shows the same view but with panel 180 closed to seal rack 100 within the temperature controlled interior area. FIG. 4 shows a diagonal view of an embodiment similar to that shown in FIGS. 2 and 3 but with two ducts 400 and 410 shown on one side. Of course other ducts (not shown) could be present on the opposite side or back. FIG. 5 shows a top view of a four-duct embodiment with ducts 400, 410, 500, and 510 shown.

Figure 6:
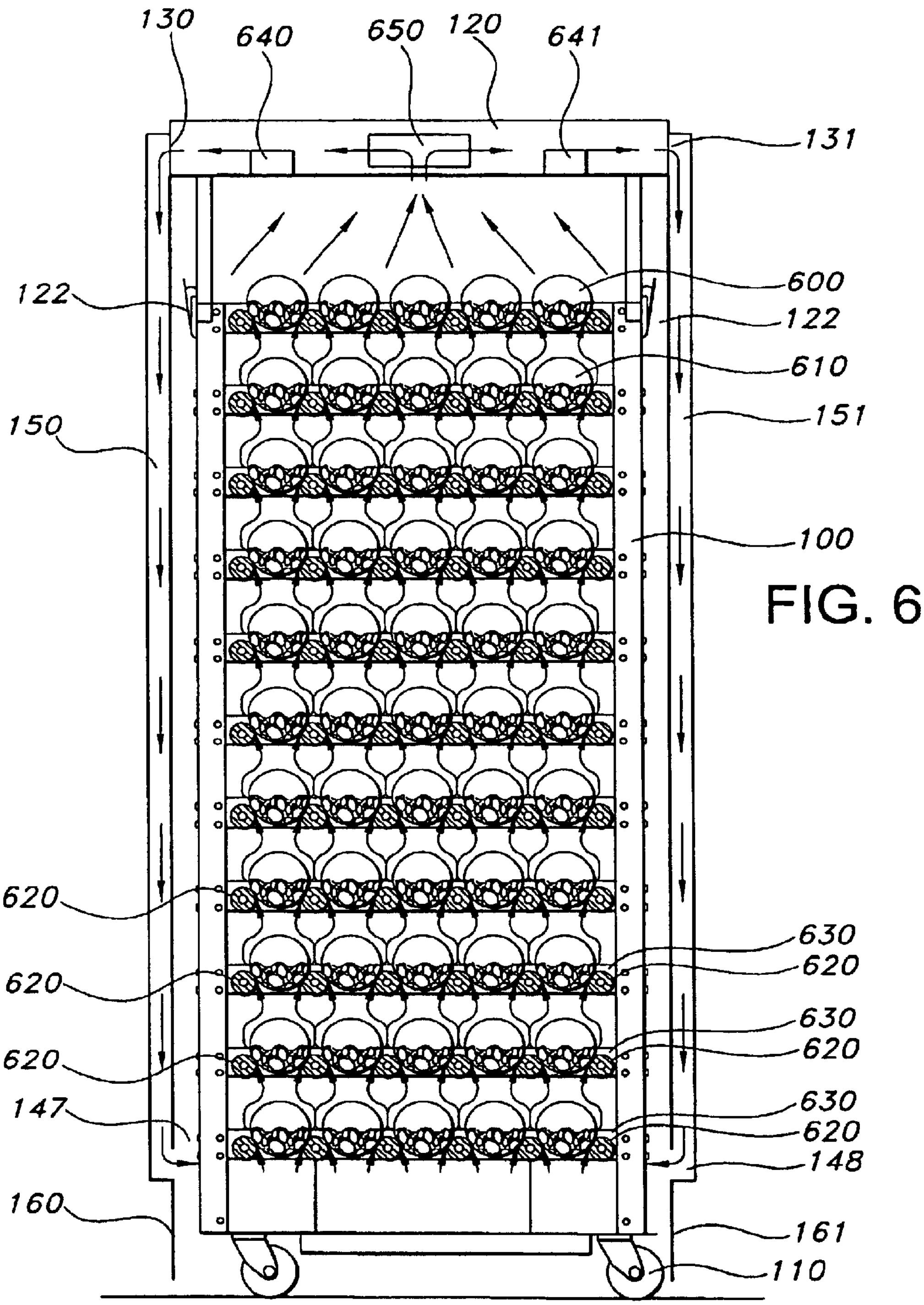
FIG. 6 is a partial cross-sectional front view of the present invention disposed around a rack having bottles disposed therein.

FIG. 6 shows a partial front cross-sectional view of a preferred device according to the present invention. Bottles 600 are placed within rack 100. Each bottle 600 contains reaction material 610, such as cells and medium, perhaps for cell culture, or fermentation or the like. This embodiment shows 55 bottles with medium. Rack 100 is also shown having rollers 620 disposed along each horizontal deck or level 630. These rollers allow the bottles 600 to be rotated during the period of reaction, which is sometimes preferred. These aspects of rack 100 are known to those skilled in the art.

FIG. 6 also shows ducts 150 and 151 which, in the preferred embodiment described above, carry warmed air from heaters 640 and 641 located in frame 120. Blower 650 is also disposed within frame 120 to pull air from the enclosed area at the top of rack 100, force it over heaters 640 and 641, and down ducts 150 and 151 where it is reintroduced into the interior area at hood duct output ports 147 and 148, as shown by the arrows in FIG. 6. Heaters 640 and 641 and blower 650 are shown only schematically in FIG. 6, but it is within the knowledge of those skilled in the art to select suitable blowers and heaters for this purpose.

In its preferred embodiment, where a heater is the temperature-controlling element, the present invention achieves heating in two ways, namely through forced air heat exchange (because of the blower) but also natural convection as the warmed air is introduced at the bottom of the rack and allowed through natural convection (albeit in addition to the forced air circulation) to rise through the rack. When required the controller activates the blower to force heated air through the enclosure. This situation takes advantage of both forced air movement and the heat transfer properties associated therewith, and also natural convection.

Figure 7:
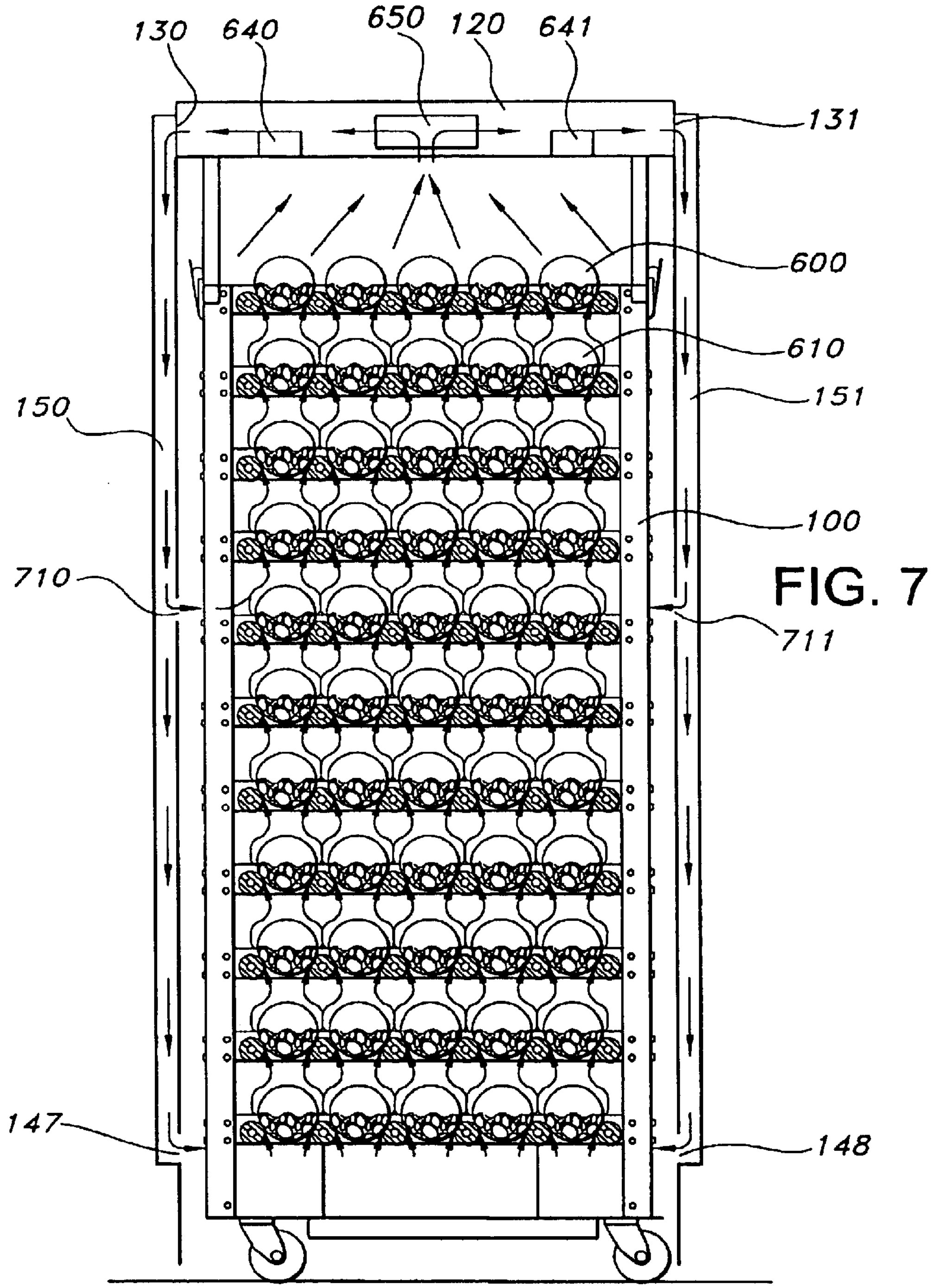
FIG. 7 is a partial cross-sectional front view of an alternative embodiment of the present invention having multiple heat inlets per duct.

FIG. 7 shows a variant of the embodiment shown in FIG. 6, namely that two hood duct output ports are used per side. Hood duct output ports 147 and 148 are joined by upper hood duct output ports 710 and 711. This embodiment allows for the warmed air stream entering each duct 150 and 151 to reach the upper bottles at a temperature warmer than it otherwise would if not for upper hood duct output ports 710 and 711 (i.e. the situation shown in FIG. 6). This embodiment allows for different temperature control schemes than that of the embodiment of FIG. 6.

The above embodiments, where the hood is suspended from a frame mounted to the top of a rack, allow the rack to be moved about even during experimentation (which may not always be desired) or between experiments, depending upon laboratory space requirements.

Another embodiment of the present invention utilizes a system where the frame is mounted directly to a wall or suspended from a ceiling and a hood is suspended therefrom. Such an arrangement allows the draping of the hood which, together with the frame, form an enclosed area into which a laboratory rack can be rolled. All other aspects of this embodiment are generally the same as those discussed above. Any number of different attachment means can be used to mount the frame to the wall or ceiling, including something as simple as bolting the frame directly to a laboratory wall or ceiling. Furthermore, other mounting systems could work, including the use of a free-standing frame disposed atop a laboratory bench or table top. When not in use, the hood can be folded up and stored away, or even simply laid atop the frame and out of the way.

One particular embodiment of this aspect is shown in FIG. 8 where a bracketing system is utilized. Here, wall anchors 810 and 811, as shown in FIG. 8A, allow frame 800 to be mounted to two brackets 812 and 813 which are in turn attached to wall anchors 810 and 811. Once frame 800, which in all other aspects is the same as that disclosed above for frame 120, including frame duct connection ports 130 and 131, is suspended from brackets 812 and 813, hood 140 can be suspended therefrom to form a sort of soft-sided, insulated closet into which a rack can be rolled.

Another particular embodiment of this aspect is shown in FIG. 8 where a hanging system is utilized. Here, ceiling anchors 879, as shown in FIG. 8D, allow frame 800 to be mounted to four threaded hangers 877 and 878 which are in turn attached to ceiling anchors 879. Once frame 800, which in all other aspects is the same as that disclosed above for frame 120, including frame duct connection ports 130 and 131, is suspended from hangers 877 and 878, hood 140 can be suspended therefrom to form a soft-sided, insulated closet into which a rack can be rolled.

Figure 8D:
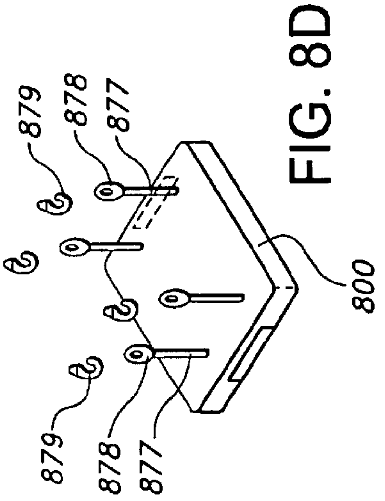
FIG. 8D is a diagonal view of an alternative embodiment of the frame according to the present invention where the frame is suspended from the ceiling.
Figure 8C:
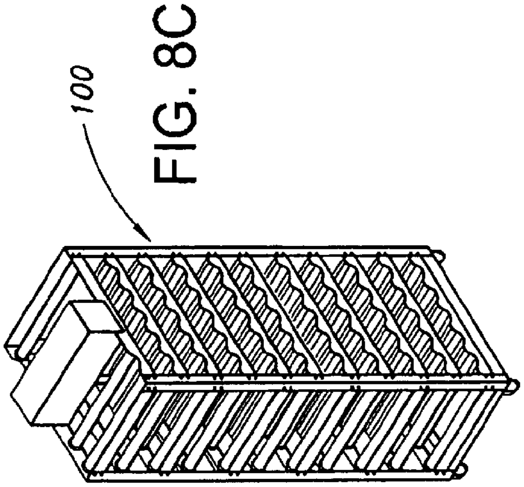
FIG. 8C is a diagonal view of a rack which can be used with the present invention.
Figure 8B:
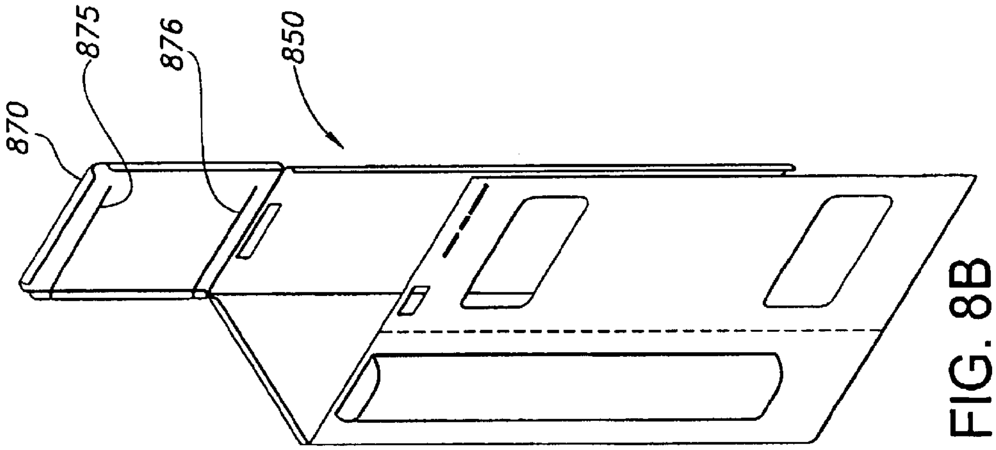
FIG. 8B is a diagonal view of an alternative embodiment of the hood according to the present invention for use with a wall-mounted frame.
Figure 8A:
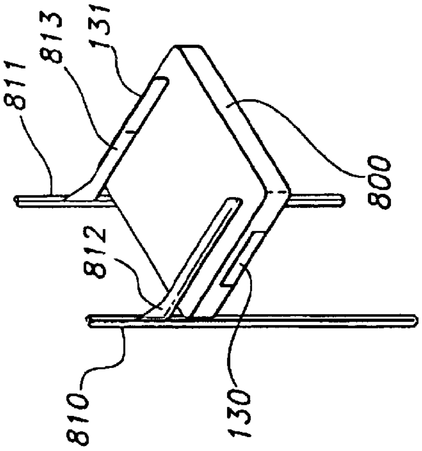
FIG. 8A is a diagonal view of an alternative embodiment of the frame according to the present invention where the frame is wall-mounted.

FIG. 8C shows rack 100, which is the same as that of FIG. 1A. FIG. 8B shows a hood 850, which is substantially the same as that shown in FIG. 1C, except for the top piece.

FIG. 1C shows top 170. FIG. 8B shows top 870 with two grooves 875 and 876 formed therein. These are formed to allow room in top 870 when it is closed over brackets 812 and 813. Of course, when frame 800 is mounted to the wall using some means other than the brackets, these grooves may not be necessary.

Advantages of the present invention include that fact that the soft-sided incubator hood embodiment can be made of a heat-reflective soft curtain or other thermally insulating material. The hood, or soft side curtain provide equal or superior thermal insulation and convenience as compared to known sheet metal cabinets. The soft sides can be made of one material or a combination or layers of materials, not limited to but including, flexible plastics, cloth, metal foil, fiberglass, multi-layer polymeric fabrics, or other man made materials. The preferred materials of construction would be bio-compatible and carry a UL94-VTM fire rating. One possible method a shown in FIG. 1D might include three layers. Outer layer 190 could be constructed of Snyder Manufacturing Weatherspan® 13 oz PVC, the middle layer 191 could be EN Murray Pyrell acustical foam, a thermally insulating layer, and the inner layer 192 could be constructed of Deerfield Urethane PT9101A PVC.

Such a configuration as described above also allows for considerable weight reduction over known units which results in lower storage and transportation costs. When not in use, the soft curtain allows the system to be space-minimized such that a very small space is consumed. The unit can be rolled or folded up so that the only significant remaining volume is that occupied by the frame/air handling unit. In addition, the soft incubator can conform to many sizes and shapes of cell culture apparati and racks, from roller apparati to various bench top units. For the bench top units an outer frame could be added to support the control frame and soft side curtains.

Other embodiments could take advantage of more than just temperature control. In such cases, humidity could also be controlled with suitable handling units in the frame. Although most of the above disclosure centered on warming the environment, cooling could also be accomplished. Furthermore, controlled atmospheres such as $CO_2$ control or oxygen introduction could also be accommodated.

The control frame consists of an outer protective shell with mounting adaptations which house a means to heat air and move the air through the enclosure both activated by either mechanical or electronic controls and an interface to adjust and monitor the results. The outer protective shell and mounting system could consist of a strong stiff material, which is strong enough to protect the internal components from damage and support the weight of the soft curtain. It could be made of any of the following materials: plastics, wood, metal, or fiberglass.

The air is heated or cooled by turning on a heater or compressor, which may be any of the following types: coil, wire resistance, or fin strip types. The typical heater may have in independent high temperature cut-off for safety. One possible selection could be a fin strip heater similar to a Caloritech/Wellman model FS102X.

The air flow and heat requirements may vary depending on the size of the enclosure and application. The air may be moved by any of the following methods: fan, blower, bellows, or a compressor. A typical fan would be similar to an EBM model R2E220, which provides air flow ranging from 200 to 1000 cubic feet per minute. The larger the rack and the higher the temperature requirement, the larger the demand on the air handling system. The temperature and movement of the air needs to be controlled to achieve the desired results within the enclosure. This is achieved via mechanical and/or electronic switches and controls, such as an ATHENA PID Temperature controller model #M400. This aspect of the present invention, however, is defined by parameters known to those skilled in the art.

Also included as a part of the invention is a method of controlling the temperature of a reaction. The method comprises the steps of first suspending a soft hood from a frame to form an enclosed area below the frame, and then inserting a reaction vessel or rack into the enclosed area. Then air is brought to a first desired temperature within the frame and is passed from the frame down to the bottom of the suspended soft hood and into the enclosed area. The air introduced at the bottom is brought up through the rack or vessels and is taken back into the frame where it is again brought to the first desired temperature. This process continues until the desired reaction within the vessels is complete. In a preferred application of the method, the air is warmed in the frame to a temperature higher than the surrounding temperature.

Accordingly, while illustrated and described herein with reference to certain specific embodiments, the present invention is not intended to be limited to the embodiments and details shown. Rather, the appended claims are intended to include all embodiments and modifications which may be made in these embodiments and details, which are nevertheless within the true spirit and scope of the present invention.

What is claimed:

1. A cover for a rack to control the temperature of the contents of the rack comprising:

a frame having a temperature-controlling element, said frame adapted to be disposed above a rack;

a soft hood having a bottom, said hood extending downward from said frame; and a duct fluidly connecting said temperature-controlling element to the bottom of said hood.

2. The cover of claim 1 wherein said temperature-controlling element is a heater.

3. The cover of claim 1 wherein said temperature-controlling element is a refrigeration device.

4. The cover of claim 1 further comprising a blower in said frame.

5. The cover of claim 1 wherein said frame has four sides and said hood has four sides, and each said hood side attaches to a respective frame side.

6. The cover of claim 1 wherein said frame is adapted to be attached to a wall or suspended from a ceiling.

7. The cover of claim 1 wherein said frame is adapted to be disposed on top of a laboratory bottle rack.

8. The cover of claim 1 wherein said hood has an openable front panel to allow insertion and removal of a rack.

9. The cover of claim 1 wherein said hood is comprised of a multi-layered material.

10. The cover of claim 9 wherein said hood is three-layered and one of the three layers is a thermal insulation.

11. The cover of claim 1 wherein said hood is one piece.

12. The cover of claim 1 comprising two ducts.

13. The cover of claim 1 wherein said duct is disposed outside of said hood.

14. A method of controlling the temperature of a reaction comprising the steps of:

(a) suspending a flexible hood from a frame to form an enclosed area below the frame;

(b) inserting a reaction vessel into the enclosed area;

(c) bringing air within the frame to a first desired temperature;

(d) passing the air from the frame to the bottom of the hood and into the enclosed area;

(e) taking up the air from the enclosed area at the top of the hood and bringing it back to said first temperature in the frame; and (f) repeating steps (d) and (e) until a desired reaction is complete.

15. The method of step 14 wherein step (c) comprises warming air within the frame.

* * * * *